US011305073B2

(12) United States Patent
Stenzler et al.

(10) Patent No.: US 11,305,073 B2
(45) Date of Patent: Apr. 19, 2022

(54) DEVICE AND METHOD FOR TARGETED DELIVERY OF AEROSOLIZED PARTICLES TO THE LUNGS

(71) Applicant: Monitored Therapeutics, Inc., Dublin, OH (US)

(72) Inventors: Alex Stenzler, Long Beach, CA (US); Steve Han, Huntington Beach, CA (US); Martin Stegenga, Seal Beach, CA (US)

(73) Assignee: Monitored Therapeutics, Inc, Dublin, OH (US)

( * ) Notice: Subject to any disclaimer, the term of this patent is extended or adjusted under 35 U.S.C. 154(b) by 367 days.

(21) Appl. No.: 16/269,766

(22) Filed: Feb. 7, 2019

(65) Prior Publication Data

US 2019/0240428 A1    Aug. 8, 2019

Related U.S. Application Data

(60) Provisional application No. 62/627,330, filed on Feb. 7, 2018.

(51) Int. Cl.
*A61M 11/00* (2006.01)
*A61M 15/00* (2006.01)
*A61M 16/00* (2006.01)

(52) U.S. Cl.
CPC ......... *A61M 11/005* (2013.01); *A61M 11/001* (2014.02); *A61M 15/0016* (2014.02); *A61M 15/0021* (2014.02); *A61M 15/0085* (2013.01); *A61M 15/002* (2014.02); *A61M 15/0015* (2014.02); *A61M 15/0018* (2014.02); *A61M 2016/0021* (2013.01); *A61M 2016/0027* (2013.01); *A61M 2016/0033* (2013.01); *A61M 2205/3334* (2013.01); *A61M 2205/3553* (2013.01); *A61M 2205/3569* (2013.01); *A61M 2205/3592* (2013.01); *A61M 2205/52* (2013.01); *A61M 2205/581* (2013.01);
(Continued)

(58) Field of Classification Search
CPC .............. A61M 11/001; A61M 11/005; A61M 15/0015; A61M 15/0016; A61M 15/0021; A61M 15/002; A61M 2016/0021; A61M 2205/3553; A61M 2205/583; A61M 2205/587
See application file for complete search history.

(56) References Cited

U.S. PATENT DOCUMENTS

2003/0140921 A1* 7/2003 Smith .................... B65D 1/095
128/200.14
2003/0205229 A1* 11/2003 Crockford ......... A61M 15/0088
128/204.23
(Continued)

*Primary Examiner* — Timothy A Stanis
(74) *Attorney, Agent, or Firm* — Riverside Law LLP (57) ABSTRACT

A nebulizer device includes an air intake port positioned downstream of a nebulizer element, and a mouthpiece positioned upstream of the nebulizer element. A flow sensor is coupled to a controller. The controller is configured to integrate an inhaled air flow signal received from the flow sensor for determining an inhaled air volume. The controller is also configured to turn on the nebulizer element when the inhaled air volume reaches a first predetermined threshold, and turn off the nebulizer element when the inhaled air volume reaches a second predetermined threshold. A method for targeted delivery of aerosolized particles to the lungs is also disclosed.

19 Claims, 8 Drawing Sheets

(52) U.S. Cl.
CPC . *A61M 2205/583* (2013.01); *A61M 2205/587* (2013.01); *A61M 2205/6018* (2013.01); *A61M 2205/6027* (2013.01); *A61M 2205/6045* (2013.01); *A61M 2205/8206* (2013.01); *A61M 2205/8237* (2013.01); *A61M 2209/086* (2013.01)

(56) References Cited

U.S. PATENT DOCUMENTS

| | | | | |
|---|---|---|---|---|
| 2005/0121033 | A1* | 6/2005 | Starr | A61M 16/1065 128/204.18 |
| 2005/0155602 | A1* | 7/2005 | Lipp | A61M 15/0065 128/203.12 |
| 2010/0282247 | A1* | 11/2010 | Kadrichu | A61P 19/04 128/200.14 |
| 2011/0108025 | A1* | 5/2011 | Fink | A61M 16/105 128/200.16 |
| 2013/0327323 | A1* | 12/2013 | Rubin | A61M 16/1055 128/200.18 |
| 2019/0290879 | A1* | 9/2019 | Kern | A61M 15/0086 |

* cited by examiner

```
┌─────────────────────────────┐
│ Determine deposition identity from │
│ removable storage container 201    │
└─────────────────────────────┘
              │
              ▼
┌─────────────────────────────┐
│ Measure inspiratory flow and       │
│ integrate to determine inspiratory │
│ volume 202                         │
└─────────────────────────────┘
              │
              ▼
┌─────────────────────────────┐
│ Activate nebulizer element based   │
│ on deposition identity and         │
│ inspiratory volume 203             │
└─────────────────────────────┘
              │
              ▼
┌─────────────────────────────┐
│ Deactivate nebulizer element       │
│ based on deposition identity and   │
│ inspiratory volume 204             │
└─────────────────────────────┘
```

FIG. 8

DEVICE AND METHOD FOR TARGETED DELIVERY OF AEROSOLIZED PARTICLES TO THE LUNGS

CROSS-REFERENCE TO RELATED APPLICATIONS

This application claims priority to U.S. provisional application No. 62/627,330 filed on Feb. 7, 2018, incorporated herein by reference in its entirety.

BACKGROUND OF THE INVENTION

Effective drug delivery to patients is an important aspect of any successful drug therapy. Certain therapies rely on pulmonary delivery techniques, which includes inhalation of a pharmaceutical formulation by the patient so that the drug or active agent within the formulation can reach the lungs. Pulmonary delivery techniques can be particularly advantageous for treating certain respiratory related ailments since it allows for selective delivery of pharmaceutical formulations to the airways. Pulmonary delivery techniques also have been known to cause less side effects than traditional systematic administration.

The efficacy of drug delivery can be improved by targeting aerosolized medication to certain areas of the lungs. For example, U.S. Pat. No. 8,534,277 to Stenzler et al. titled "Device, system and method for targeting aerosolized particles to a specific area of the lungs" describes a system that can target a specific area of the lungs by altering aerosol parameters, such as volume, particle size, timing and flow rate. For example, the system introduces particle free air for a first predefined time period, then introduces a certain amount of aerosolized particles, followed by a second predefined period of aerosol particle free air. The object of introducing particle free air in the first predefined period is to direct air to the lower regions of the lungs. The object of the second time period of particle free air is to clear the upper region and extrathoracic airway region, respectively, (e.g., mouth, pharynx, and trachea) of the lungs to thereby drive the aerosol bolus to the central region (bronchial) or peripheral region of the lungs. In addition to initiating drug delivery based on time, certain prior art devices can also initiate drug delivery based on detecting a threshold inhalation flow volume. In these systems, once the nebulizer is turned on, the duration of drug delivery is based on delivering a fixed bolus or fixed volume of drug over a fixed time interval.

However, there are certain disadvantages to the prior art systems described above. For example, once drug delivery is triggered, if a patient is breathing slower and takes more time to reach the stopping volume, the nebulizer will deliver excessive amounts of drug since delivery is based on a fixed time interval. Conversely, if the patient is breathing fast, the nebulizer will continue to deliver drugs while the patient is exhaling, which is wasteful and ineffective, while the patient receives less than the desired dosage.

Accordingly, there is the need in the art for an improved device that can more efficiently and effectively deliver drugs to a patient, taking into account the real-time variability of inhalation efforts among different patients, as well as the real-time variability of inhalation efforts of the same patient from breath-to-breath.

SUMMARY OF THE INVENTION

In one embodiment, a nebulizer device includes an air intake port positioned downstream of a nebulizer element, and a mouthpiece positioned upstream of the nebulizer element; and a flow sensor coupled to a controller; wherein the controller is configured to integrate an inhaled air flow signal received from the flow sensor for determining an inhaled air volume; wherein the controller is configured to turn on the nebulizer element when the inhaled air volume reaches a first predetermined threshold, and wherein the controller is configured to turn off the nebulizer element when the inhaled air volume reaches a second predetermined threshold. In one embodiment, the predetermined threshold is a patient-specific threshold. In one embodiment, the nebulizer device includes a plurality of deposition detection elements configured to mate with a plurality of deposition identification elements disposed on a removable storage container. In one embodiment, the plurality of deposition detection elements are a plurality of detection pins. In one embodiment, the plurality of deposition identification elements are a plurality of metal contacts connected to the nebulizer element. In one embodiment, the plurality of deposition identification elements are indicative of a target deposition area within lungs of a patient. In one embodiment, an opening to the removable storage container is at least partly defined by the nebulizer element. In one embodiment, the nebulizer element is a nebulizer mesh. In one embodiment, the removable storage container comprises an interior cup nested within a chamber of the storage container. In one embodiment, the interior cup is in fluid communication with the nebulizer element, and the chamber is not in fluid communication with the nebulizer mesh. In one embodiment, the flow sensor is a single fixed orifice flow sensor. In one embodiment, the flow sensor is a dual orifice flow sensor comprising a fixed orifice and a variable orifice arranged in parallel. In one embodiment, a one way valve positioned directly over the dual orifice flow sensor configured to permit airflow in an upstream direction. In one embodiment, the nebulizer device includes a drip cup positioned between the mouthpiece and the flow sensor. In one embodiment, the nebulizer device includes an exhalation valve positioned between the mouthpiece and the storage container. In one embodiment, the air intake port is positioned at a base of the nebulizer device housing. In one embodiment, the nebulizer device includes a portable power source coupled to the controller and nebulizer element, and stored within a housing of the nebulizer device. In one embodiment, the nebulizer device includes a status indicator coupled to the controller and comprising at least one of a light indicator and an auditory indicator. In one embodiment, the status indicator is configured to activate when the inhaled air volume reaches the first predetermined threshold. In one embodiment, the status indicator is configured to activate when the inhaled air volume reaches a second predetermined threshold. In one embodiment, the nebulizer device is a handheld device.

In one embodiment, a method for targeted delivery of aerosolized particles to the lungs includes the steps of determining a deposition identity from a removable storage container; measuring and integrating an inspiratory flow to determine inspiratory volume; activating a nebulizer element when the inspiratory volume reaches a first volume threshold associated with the deposition identity; and deactivating the nebulizer element when the inspiratory volume reaches a second volume threshold associated with the deposition identity.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which.

DETAILED DESCRIPTION OF THE INVENTION

It is to be understood that the figures and descriptions of the present invention have been simplified to illustrate elements that are relevant for a more clear comprehension of the present invention, while eliminating, for the purpose of clarity, many other elements found in systems and methods of targeted delivery of aerosolized particles to the lungs. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Ranges: throughout this disclosure, various aspects of the invention can be presented in a range format. It should be understood that the description in range format is merely for convenience and brevity and should not be construed as an inflexible limitation on the scope of the invention. Where appropriate, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Referring now in detail to the drawings, in which like reference numerals indicate like parts or elements throughout the several views, in various embodiments, presented herein is a device and method for targeted delivery of aerosolized particles to the lungs.

Embodiments of the device trigger drug delivery via nebulization once an inhaled volume is reached, and the device continuously nebulizes for a fixed volume of inhaled breath. This represents a significant advantage over prior art devices that nebulize over a fixed time or a fixed volume of drug. For example, if a patient inhales at a faster than normal rate and reaches the target stopping volume sooner, the embodiments of the device described herein will stop nebulizing. This is contrary to prior art devices that nebulize over a fixed time or a fixed volume of drug, and would otherwise continue to nebulize past the target inhaled volume. Thus, in the prior art, subjects can be exhaling while the device is still nebulizing, whereas embodiments of the device described herein would turn off the nebulizer if inhalation stops. Further, embodiments of the device advantageously take into account an upper airway dead space volume to clear the upper airway of aerosolized particles. Advantageously, the device is breath actuated, has an orifice flow sensor to measure inspiratory flow, and a vibrating mesh nebulizing element (which can be instantaneously turned on or off) to produce bolus aerosols. Embodiments of the reservoir medication cup also have multiple pin pairs that can inform the microprocessor as to the deposition pattern for the specific drug loaded in the reservoir. These enable the device to deliver the bolus of the aerosol to the periphery, the central airways, or both the central airways and periphery. In addition, the device can include multicolor indicators which light up the device's head and inform the user of the device status to guide the user through their treatment. Embodiments of the device can individualize and record dosages based on actual patient respiratory capability and performance of the particular patient. The device makes delivery of the drug products in the exact amounts and lung locations possible, whether central, periphery, or both or continuous on inspiration according to physician's prescriptions. Further, the device can maintain complete compliance with all HIPAA regulations and requirements, and connections such as Bluetooth enable device diagnostics that may be accessed and reviewed remotely.

Figure 1:
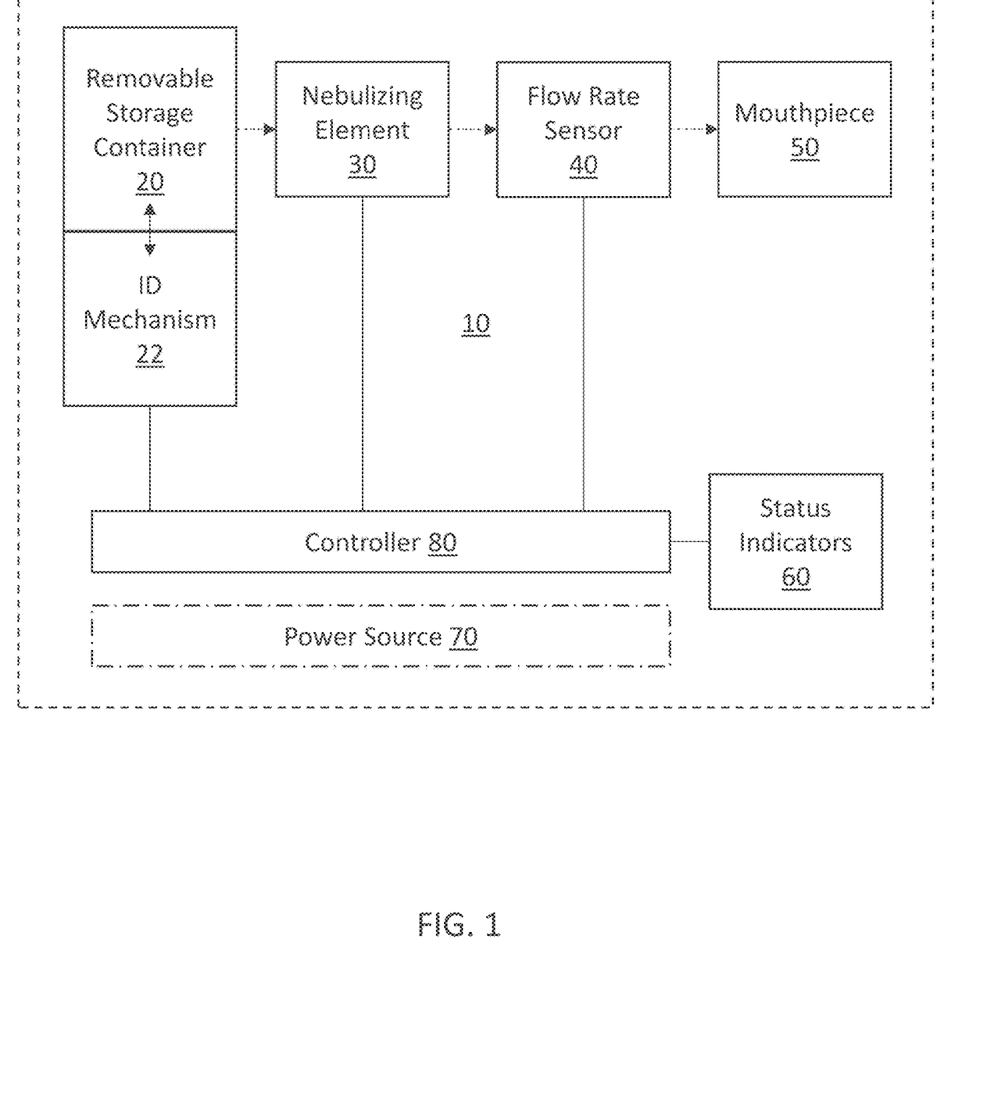
FIG. 1 is a system diagram of a nebulizer device according to one embodiment.
Figure 2:
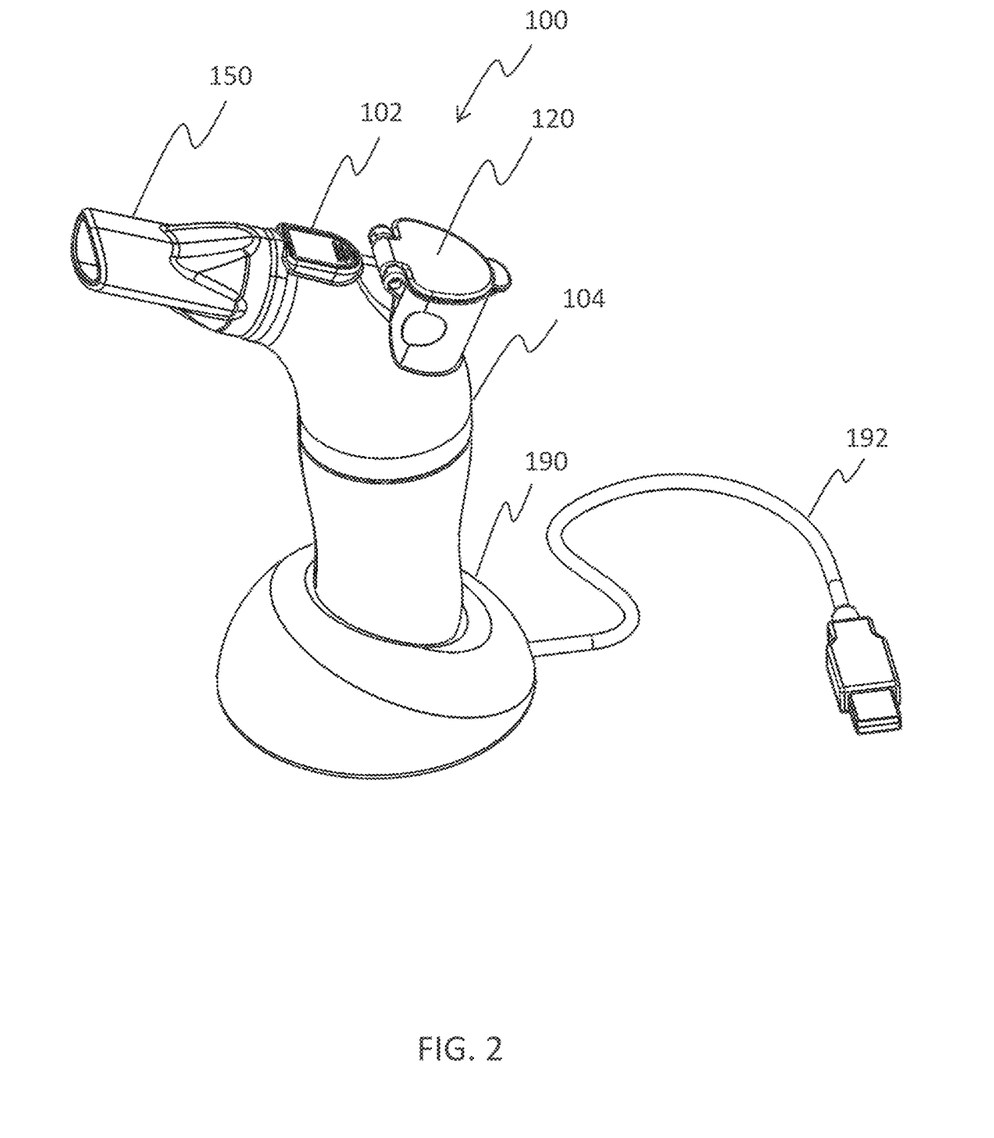
FIG. 2 is a perspective view of a nebulizer device resting in a charging base according to one embodiment.
Figure 3:
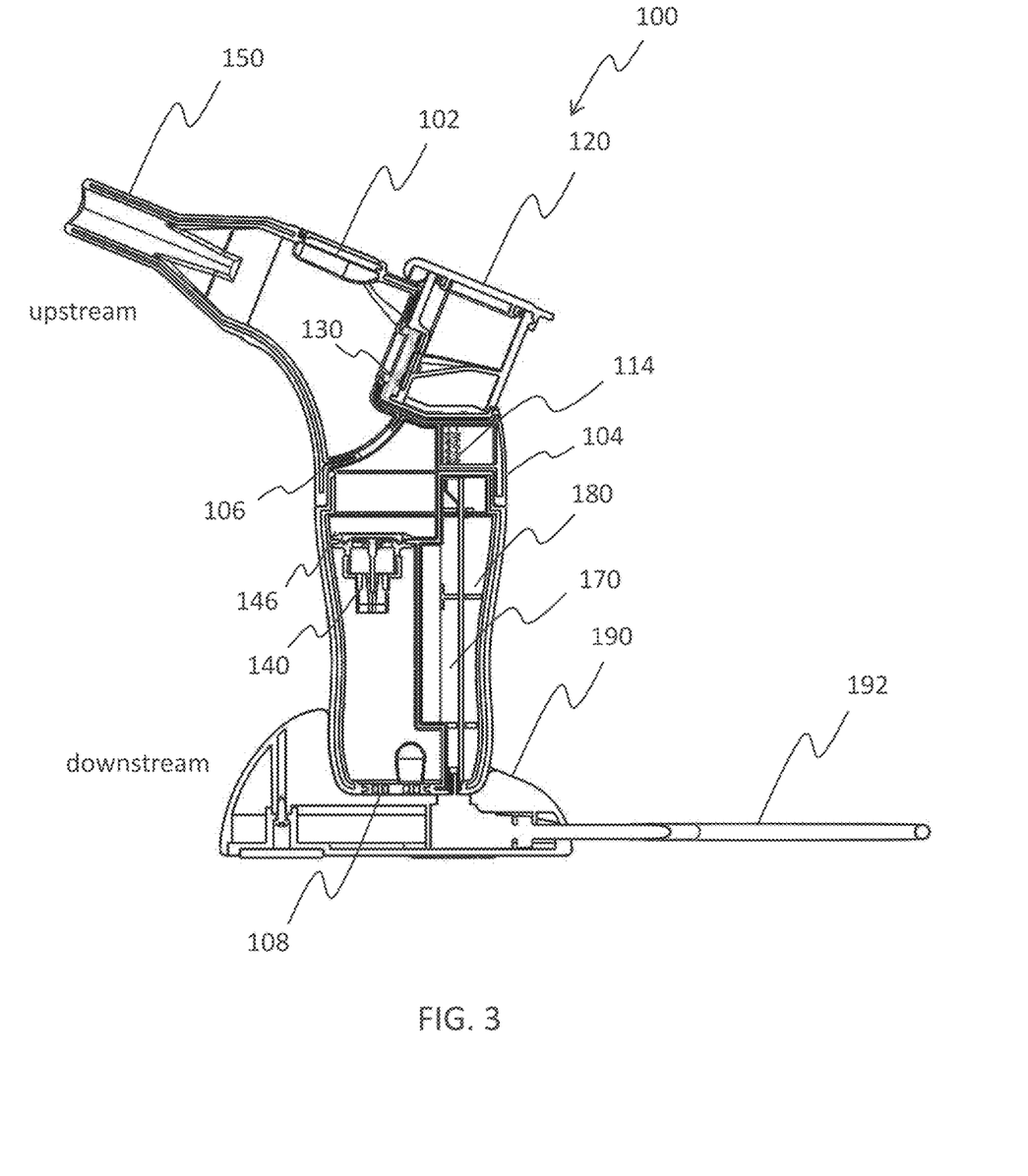
FIG. 3 is a side cutaway view of a nebulizer device resting in a charging base according to one embodiment.
Figure 4A:
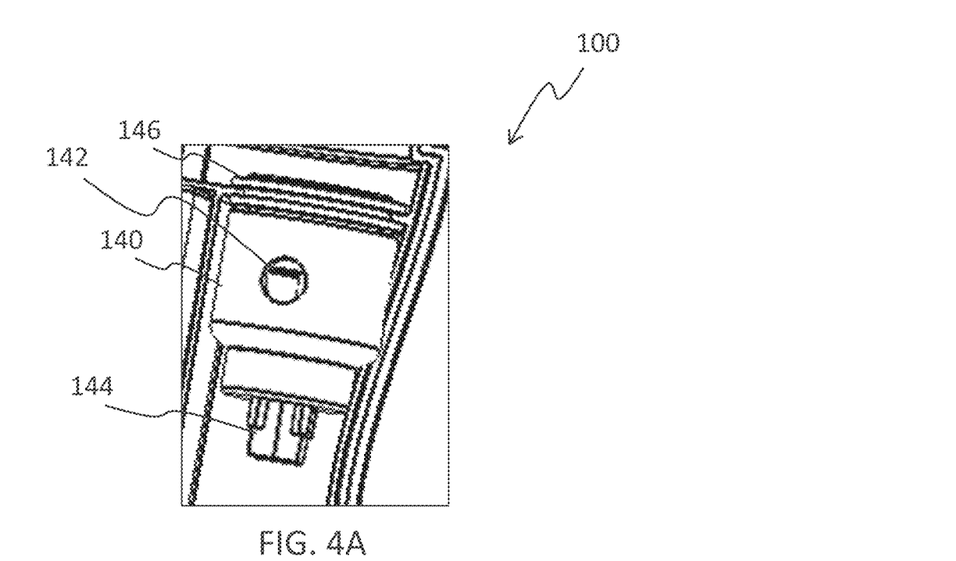
FIG. 4A is an isolated and magnified side view of a dual orifice flow sensor according to one embodiment.
Figure 4B:
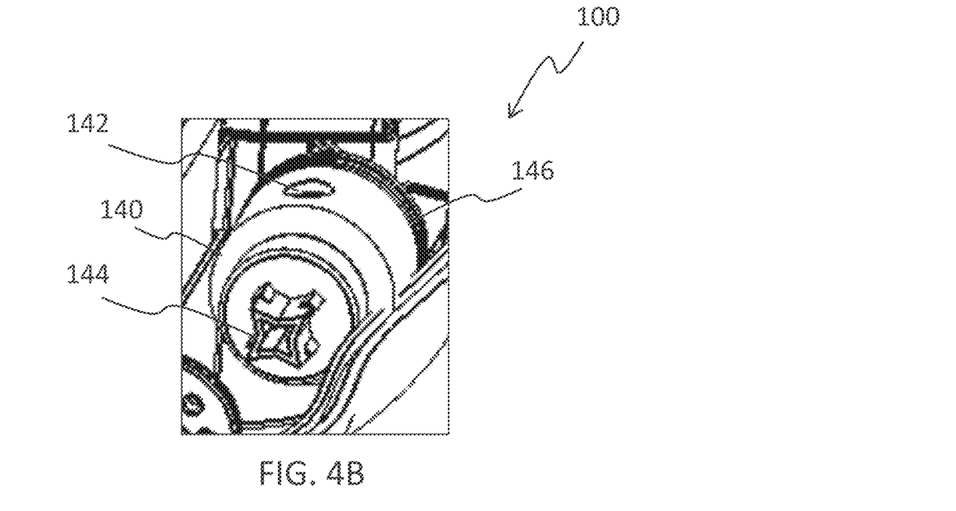
FIG. 4B is an isolated and magnified perspective view of the dual orifice flow sensor shown in FIG. 4A.

With reference now to FIG. 1, according to one embodiment, a system diagram for a handheld nebulization device 10 includes a removable storage container 20 that communicates with an ID mechanism 22. This communication between the removable storage container 20 and ID mechanism relays delivery parameters to the nebulizing element 30 via the controller 80 for purposes of delivering medication to the proper area of the lungs. In one embodiment, the ID mechanism 22 includes a series of leads that interact with a pattern of metal contacts on the storage container 20. For example, in one embodiment, the ID mechanism 22 includes a left pair of contacts (contacts 1 and 2) and a right pair of contacts (contacts 3 and 4). One of the left pair of contacts can complete a circuit with one of the right pair of contacts, identifying different values based on which combination of left-pair contacts 1 and 2 completes the circuit with right-pair contacts 3 and 4. Since different electrical signals can be associated with the different combinations of connections between the left pair of contacts (contacts 1 and 2) and the right pair of contacts (contacts 3 and 4), the pattern of metal contacts on the storage container 20 can be set to correspond with four different drug delivery parameters. The pattern of metal contacts can communicate with the nebulizing element 30 via the controller 80 so that different combinations of connections can differentiate delivery. This way, embodiments of the device can identify not only the drug, but specifically where the drug should be delivered by communicating delivery parameters to the nebulizing element 30. Communication can also be through other means understood in the art, such as in one embodiment, the storage container 20 includes a geometric structure that mechanically mates with a spring loaded pin structure on the ID mechanism 22, so that the storage container 20 acts as a mechanical key for relaying delivery parameters. In one embodiment, the nebulizing element 30 is an ultrasonic vibrating mesh that can be instantaneously turned on or off to produce bolus aerosols.

The nebulization device 10 includes a nebulizing element 30 that turns on during inhalation when drug should be introduced into the airstream. A flow rate sensor 40 which in one embodiment is a orifice flow sensor measures inspiratory flow. In one embodiment, during inspiration, the flow rate sensor 40 measures instantaneous inspiratory flow (which in certain embodiments requires a polynomial equation to calculate flow from pressure transducer) and integrates that flow to determine inspired volume. Depending on the deposition target in the lungs, the controller 80 will instruct when, within the patient's inspiration, the nebulizing element 30 should be turned on and turned off to deliver bolus aerosols to the targeted regions. In one embodiment, the device 100 can transmit its operational characteristics and data to a smartphone or tablet in real-time, and the peripheral device can in turn transmit functional data and instructions to the device 100. In one embodiment, the device 100 operates independent of a smartphone or tablet peripheral device. In one embodiment, the volume of upper airway dead space, target inspired volume and breath hold time are programmable parameters. In one embodiment, calculation of volumes at which nebulizer should turn on and off are based on these programmable parameters and an identification (e.g. via the storage container) of where the drug should be delivered in the lungs. In one embodiment, the flow rate sensor 40 is a single fixed orifice flow sensor and does not include a variable orifice component. In one embodiment, the flow rate sensor 40 is a dual orifice flow sensor including a fixed orifice and a variable orifice arranged in a parallel structure (described in more detail below with reference to FIGS. 4A and 4B). The fixed orifice provides a low resistance pressure drop and the variable orifice increases the sensitivity as the flow increases while providing mechanical effort feedback to the patient that their flows are increasing too much.

Status indicators 60 such as visual and/or audio indicators communicate with the controller 80, for example to tell the patient when to stop inhaling. In one embodiment, the status indicators are color LED lights. For example, if the goal is to deliver the drug to the central airways, the patient can be signaled to stop based on a detected trigger volume so that they won't keep inhaling to instead draw the drug into the periphery. In one embodiment, the device has a red-green-blue (RGB) LED for status indication. For example, in one embodiment, the LED blinks rapid blue while searching for pairing. In one embodiment, the LED blinks red for 5 seconds and then turns the device off if the battery is low. In one embodiment, the LED blinks green slowly when the patient can start an inhalation. In one embodiment, the LED illuminates solid green during an inhalation period. In one embodiment, the LED illuminates solid red during a breath hold period. In one embodiment, the LED turns off when the patient can exhale. In one embodiment, the LED blinks red slowly for 5 seconds when the reservoir is empty and the treatment is complete. In one embodiment, the user is able to view the RGB LED while operating the device and breathing on the mouthpiece 50. In one embodiment, the device has an audible tone generator to beep twice on pairing, once on start of breath hold and once on start of exhalation. Advantageously, embodiments of the device include indications based on detected inhaled volume to have the patient stop inhaling. Components of the device can be powered by a removable or rechargeable power source 70, such as a rechargeable battery.

With reference to FIGS. 2 and 3, a nebulizer device 100 is shown resting in a charging base 190 according to one embodiment. The nebulizer device 100 includes an external wall 104, a mouthpiece 150 for the patient to breath on, an exhalation valve 102 downstream of the mouthpiece 150, and a storage container 120 downstream of the exhalation valve 102. The device 100 is designed so that the patient can inhale and exhale over several cycles without removing the device 100 from their mouth. During exhalation, air flows out of the exhalation valve 102. There is also a one way valve 146 upstream and directly on top of the variable orifice flowmeter 140 that closes during exhalation and only permits the upstream flow of air. A drip cup 106 is positioned between the mouthpiece and one way valve to divert saliva and further protect the function of the variable orifice flowmeter 140, while also minimizing the risk for contaminating the storage container 120. During inhalation, room air flows upstream through the air intake port 108 and variable orifice flowmeter 140. The one way valve 146 is open during inhalation. A pressure transducer measures pressure at the variable orifice flowmeter 140 to calculate flow, which is then integrated by the controller 180 to volume. Deposition detection pins 114 communicate with the controller 180 to determine when the nebulizer mesh 130 should turn on or off, based on the configuration/instruction detected by the pins 114 and the volume calculated by the controller 180. In one embodiment, the nebulizer device 100 has four pins. As should be understood by those having ordinary skill in the art, the nebulizer can have 2, 3, 4, 5 or more pins, depending at least partially on the number of different delivery parameters desired by the system, and the number of pin combinations required to accommodate that number of delivery parameters. The system is powered by a rechargeable battery power source 170 that charges via contact with the charging base 190. The charging base 190 can also include a USB connection 192 for providing power or for updating firmware of the device 100.

In one embodiment, as shown with greater detail in FIGS. 4A and 4B, the variable orifice flowmeter 140 is a dual orifice flow sensor including a fixed orifice 142 and a variable orifice 144 arranged in a parallel structure. A one way valve 146 is positioned upstream and directly on top of the variable orifice flowmeter 140, in fluid communication with both the fixed orifice 142 and the variable orifice 144. The one way valve 146 closes during exhalation and only permits the upstream flow of air during inhalation. In one embodiment, the variable orifice 144 is a pressure actuated valve, such as a silicone duckbill valve or slit valve. The fixed orifice 142 provides a low resistance pressure drop while the variable orifice 144 increases the sensitivity as the flow increases while providing mechanical effort feedback to the patient that their flows are increasing too much. In one embodiment, the flowmeter 140 is strictly a fixed orifice flowmeter and does not include a variable orifice component.

Figure 5:
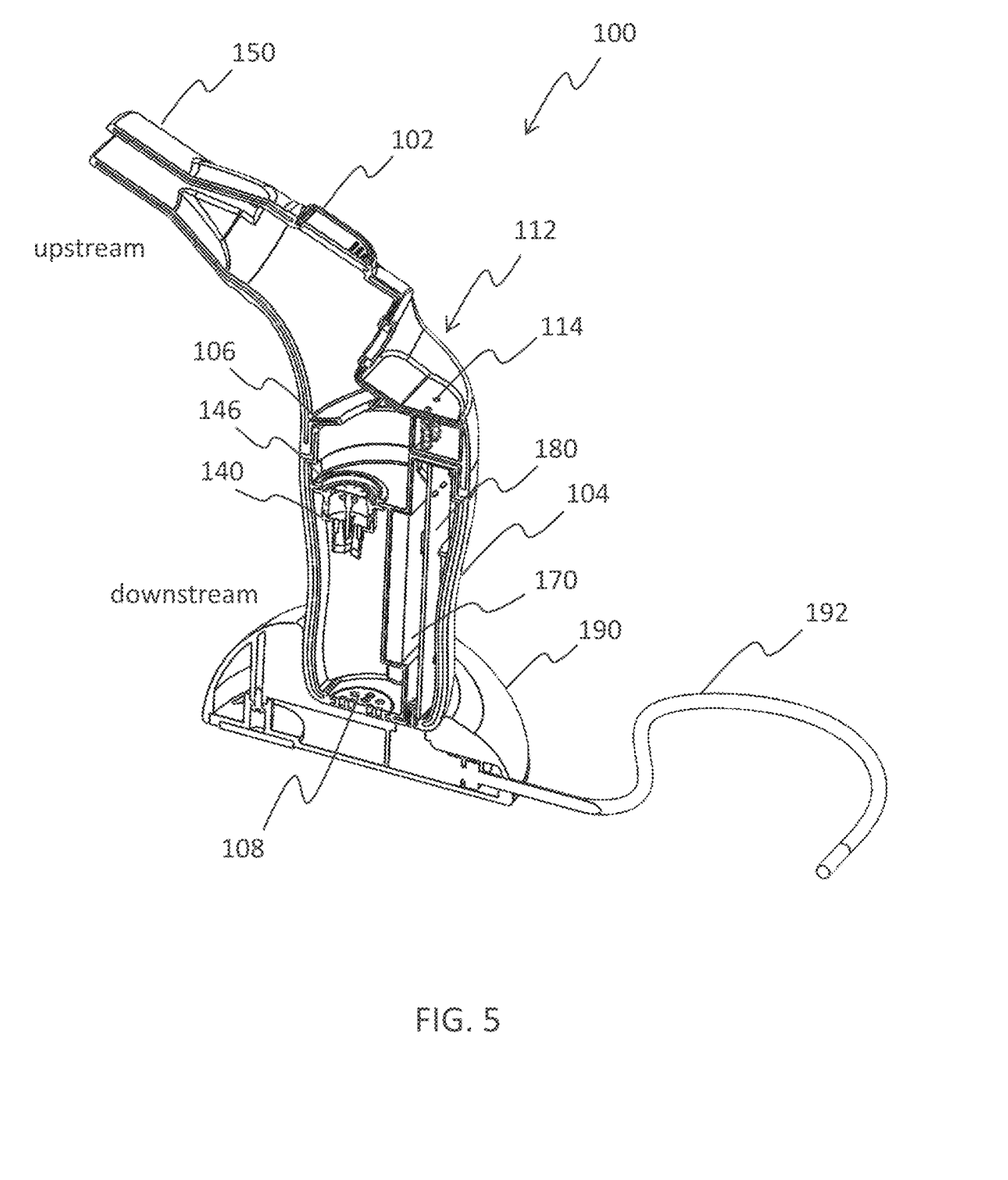
FIG. 5 is a perspective cutaway view of a nebulizer device resting in a charging base with the storage container removed from the storage container seat according to one embodiment.
Figure 6:
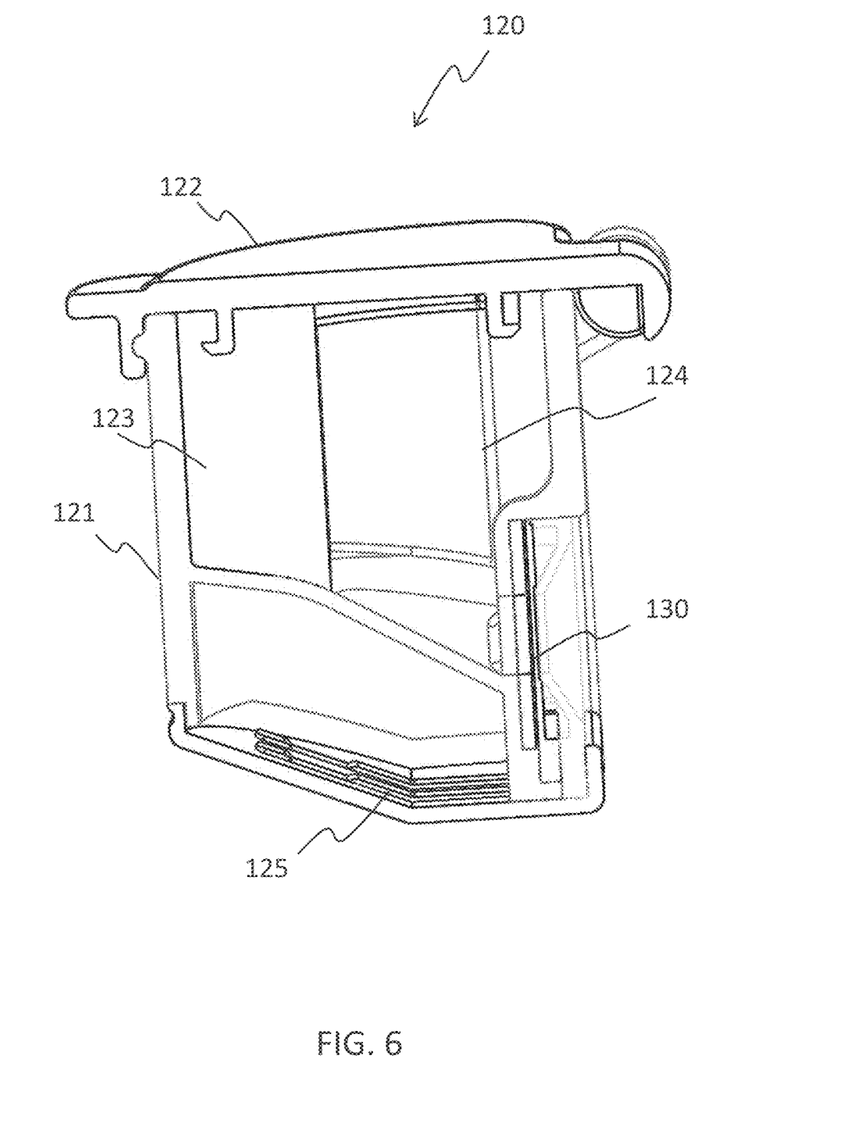
FIG. 6 is a side cutaway view of a storage container according to one embodiment.
Figure 7A:
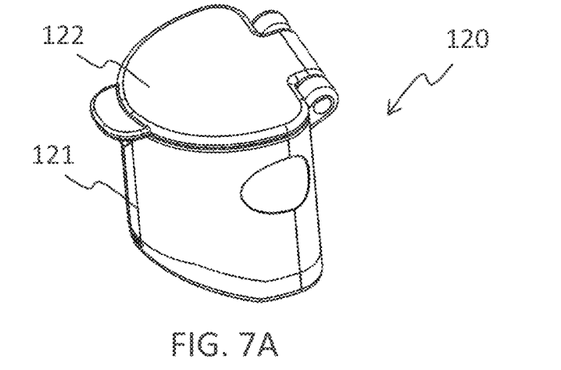
FIGS. 7A-7C are alternate perspective view of a storage container according to one embodiment.
Figure 7B:
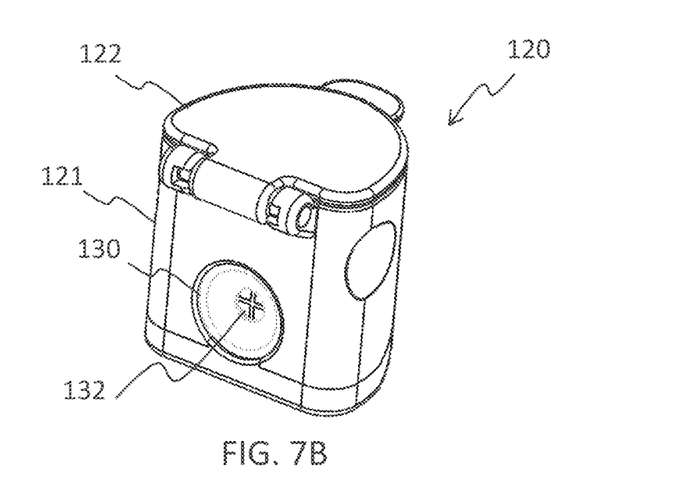
Figure 7C:
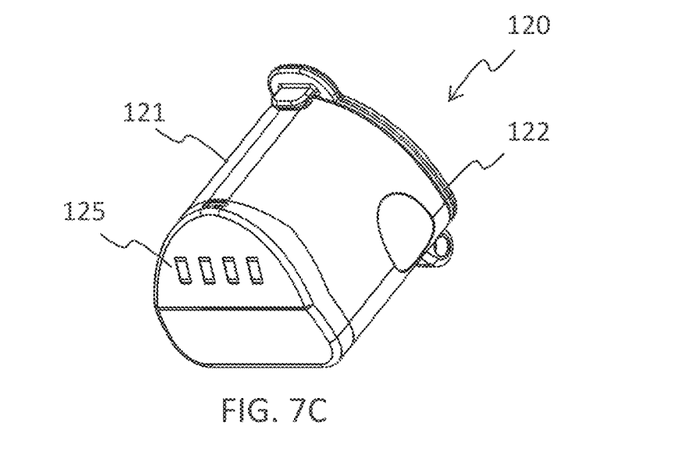

With reference now to FIG. 5, the nebulizer device 100 is shown with the storage container 120 removed from the storage container seat 112. Deposition detection pins 114 are shown in a bottom portion of the storage container seat 112. As illustrated, the deposition detection pins 114 access the storage container seat 112 so that they can mate with the corresponding deposition identity pins 125 connected to the nebulizer mesh 130 of the storage container 120, as illustrated in FIGS. 6-7C. As described above, the pin arrangement can include a left pair of contacts (contacts 1 and 2) that completes a circuit with a right pair of contacts (contacts 3 and 4). Since different electrical signals can be associated with the different combinations of connections between the left pair of contacts and the right pair of contacts, the pattern of contacts on the storage container can be set to correspond with different drug delivery parameters. With reference now to FIGS. 6-7C, the storage container 120 features multiple deposition identity pins 125 connected to the nebulizer mesh 130 and keyed to the desired target in the lungs for the patient and/or medicament that will be stored in the storage container. The storage container includes a housing 121, a lid 122 for accessing the interior chamber 123 of the housing 121, and an interior cup 124 disposed within the interior chamber 123. A nebulizer mesh 130 covers an opening 132 to the housing 121. In one embodiment, the storage container 120 includes an interior cup, or what could be referred to as a "cup within a cup". The medications typically come in a prefilled ampule that may contain for example between 2 and 5 mL. If the physician prescribes 1 mL or 3 mL, it could be difficult for some patients to place the exact amount into the cup, even with visual lines on the cup. Therefore certain embodiments include a series of insert interior cups 124 that limit the volume of liquid in front of the nebulizing mesh and pouring in more medication would cause it to overflow into the storage container chamber 123. Medication in the storage container chamber 123 will simply be retained for later use or discarding. Advantageously, the medication in the storage container chamber 123 will not be in communication with the mesh for aerosolization, and the patient avoids unintentional overmedication that commonly occurs from loading error.

Figure 8:
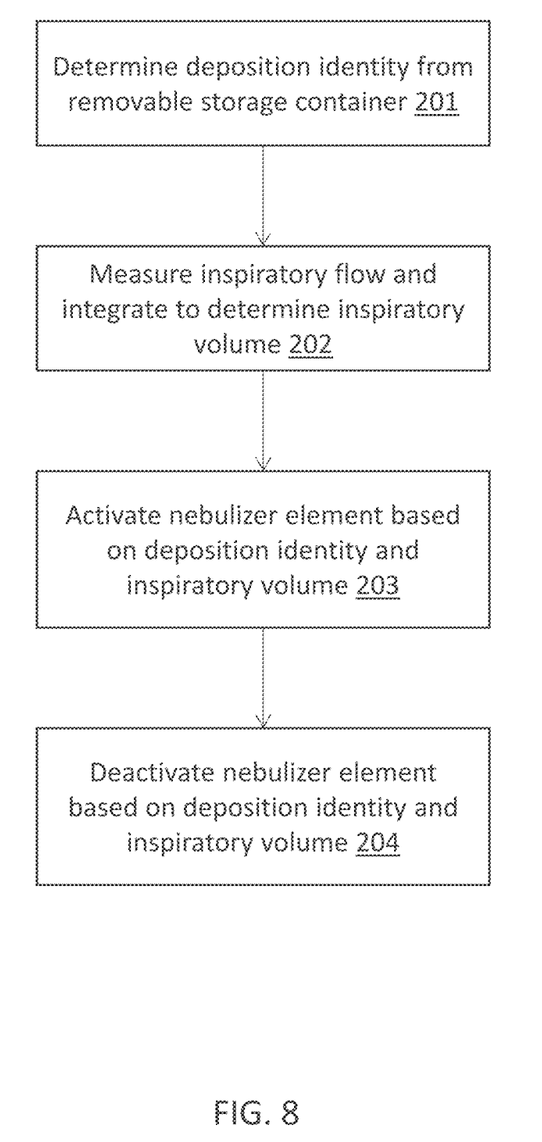
FIG. 8 is a flow chart of a method for targeted delivery of aerosolized particles to the lungs according to one embodiment.

A method for targeted delivery of aerosolized particles to the lungs 200 according to one embodiment is shown in the flow chart of FIG. 8. First, a deposition identity is determined based on a characteristic of a storage container 201. The deposition identity is based at least partially on a deposition target within the lungs of the patient. Next, inspiratory flow is measured from the patient's inhalation effort, and this value is integrated to determine total inspiratory volume 202. Based on the previously determined deposition identity and the calculated inspiratory volume, the nebulizer is activated once the appropriate first threshold is triggered 203. Finally, also based on the previously determined deposition identity and the calculated inspiratory volume, the nebulizer is deactivated on the appropriate second threshold is triggered 204.

Experimental Examples

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

In one example control process, the parameters that would be used by the nebulizer to control the nebulization include:

IV—Predicted/targeted inspired volume (Range 100-5000 mL, Default 800 mL); DS—Upper airway clearance volume (oropharyngeal volume) (Range 20-300 mL, Default 150 mL); BH—Breath-hold time (Range 0 to 9 seconds, Default 0.5 seconds); BI—Breath Interval (range 3 to 8 seconds, Default 4 seconds) and Drug Deposition target (periphery, central, both, or continuous).

The first three parameters (IV, DS and BH) have default settings while the deposition target is determined by the medication reservoir selected. The settable parameters are stored in non-volatile RAM and can be changed via the Bluetooth radio by the operator through the smartphone or tablet application. Once changed, these settings will remain as set in the RAM until changed again.

During inspiration, the nebulizer measures instantaneous inspiratory flow (requires polynomial equation to calculate flow from pressure transducer) and integrates that flow to inspired volume. Depending on the deposition target, the nebulizer will determine when, within the patient's inspiration, that the nebulizer should be turned on and turned off to deliver bolus aerosols to the targeted regions.

The nebulizer will determine the volume at which the nebulizer is turned on and turned off based on the following parameters:

1. For peripheral deposition: Nebulization started immediately upon detection of inspiration and turns off once the inspired volume reaches the set IV×0.5.

2. For central deposition: Nebulization starts when the volume reaches (IV−DS)×0.5 and stops when the inspired volume reaches IV−DS−100 mL.

3. For depositing in both: Nebulization starts immediately upon detection of inspiration and turns off once the inspired volume reaches IV−DS−100 mL.

The DAD shall have an audible tone generator to beep twice on pairing, once on ready for inhalation and once on start of breath hold.

The operational steps for the nebulizer are as follows:

1. Turn on power. (Note: Press and holding the power button turns system off)

2. Check battery level.

3. If battery is above a threshold voltage, LED rapidly blinks blue while searching for application pairing.

a. Upon pairing tone generator beeps twice and LED turns solid green.

b. After 30 seconds of searching without finding the targeted Bluetooth radio, change to a slow blink green and then read the drug container pins and go to inhalation ready.

4. If battery is low, LED rapidly blinks red and the tone generator beeps three times, transmits the low battery status to the application and then turns off.

5. Microprocessor reads the set DS, IV, s2 BI and BH.

6. Microprocessor reads the reservoir pins to determine the targeted region.
   a. Calculates the nebulizer start and stop volumes.
7. LED blinks green slowly and the tone generator beeps once when the patient can start an inhalation.
8. As patient inhales, LED turns solid green, transmits an inhalation flag, and microprocessor integrates flow to volume.
   a. Transmit continuous volume to application.
   b. Turns nebulizer on and off at the calculated volumes.
   c. At the targeted IV, transmit an IV flag, the audio tone beeps once and the LED will turn red for the duration of the BH time and then the LED will turn off.
9. The LED will turn blinking green again and the tone generator will beep once after the BI has timed out to indicate when another breath is ready to be taken and transmit an "inhalation" flag.
10. Once the microprocessor receives a signal that the reservoir is empty.

a. The microprocessor should transmit the treatment data consisting of the duration of the treatment and the number of breaths.

b. Then the LED should blink red for 5 and the tone generator will beep three times and the device should turn off.

Variations to the control process can for example include: In one embodiment, an optional operational process could include a learning mode whereby the first few breaths (e.g. five breaths) are taken without targets or nebulization. The average of these five breaths is then used to determine the target inhaled volume and the aerosolization timing determined based on that volume. In one embodiment, the microprocessor will monitor the nebulizer electronics for error codes, battery status, failures, empty drug container, etc., and transmit these to the application. In one embodiment, if inspiration stops during the expected inspiratory time, the nebulization will stop. In one embodiment, the average of actual inspired volumes from the current treatment should replace the target IV in the non-volatile RAM for the next treatment. In one embodiment, treatment parameters such as BH, starting IV, BI, and DS can be programmed by using the software application. In one embodiment, firmware is upgraded via the USB connector. In one embodiment, when the device is placed in the charging station, LED indicators can be turned on white until the battery level is above a threshold voltage and then the LED should be turned off.

In one example, during delivery mode, a pairing device such as a mobile or handheld smart device pairs with the controller of the nebulizer using a pre-configured pairing address such as a media access control (MAC) address. On successful pairing, the nebulizer controller collects patient and specific delivery settings from the paired device and both operate paired. On unsuccessful pairing, the nebulizer controller continues using the last programmed delivery settings or a default delivery setting and operates unpaired. Starting operation, the controller of the nebulizer activates an aerosolization mode and starts the detection of inhalation. The nebulizer indicates the start of inhalation. The nebulizer then activates the breath hold period per the user setting upon inhalation. Next, the nebulizer then starts a timer at the end of the breath hold period per the breath hold time user setting. Next, the nebulizer indicates it is ready for the start of a new breath when the timer reaches the breath interval time per user setting. The nebulizer stops aerosolization if inspiration stops during the expected inspiratory time and starts a breath hold period. The nebulizer continuously transmits the status of the aerosolization to the paired device throughout the process.

Additional functionality of the nebulizer in one example includes: the controller turns the nebulizer off when the battery level is below the requirement for delivery of a time duration treatment, e.g. a fifteen minute treatment; the controller of the nebulizer monitors the nebulizer electronics for error codes, battery status, failures, etc. and transmit these to the paired device; the controller of the nebulizer stores the inhaled volumes for each breath during the treatment and calculates the average inhaled volume; and the controller of the nebulizer replaces the target inhaled volume with the averaged inhaled volume from the previous treatment.

In one example, the controller interacts with the drug container to read the drug container information off a 4 pin sensing mechanism; send the drug container information to a paired Bluetooth device upon request; check the drug container pins to determine the aerosol delivery mode; stop aerosolization and turn off the nebulizer when it is detected that the drug container is empty; and prohibit aerosolization if the drug container is not detected or cannot read a proper pin combination.

In one example, the aerosol delivery mode is set on the controller to utilize a pressure sensor to calculate flow in mL/minute based on a polynomial equation or lookup table, and integrate the flow to calculate volume in mL. In one example, the aerosol delivery mode is set on the controller based on received aerosolization related specifications from the paired Bluetooth device, such as: dead space volume (Range 20-300 mL) and default value 150 mL; target inhaled volume (Range 100-5000 mL) and default value 800 mL; breath hold time (Range 0-9000 ms) and default 500 ms; breath interval time (Range 3000-8000 ms) (i.e., period from end of breath hold to ready for next inhalation) and default 4000 ms.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention.

What is claimed is:

1. A nebulizer device comprising:

an air intake port positioned downstream of a nebulizer element, and a mouthpiece positioned upstream of the nebulizer element; and a flow control sensor coupled to a controller, the flow control sensor comprising a fixed orifice and a variable orifice arranged in parallel;

wherein the controller is configured to integrate an inhaled air flow signal received from the flow control sensor for determining an inhaled air volume;

wherein the controller is configured to turn on the nebulizer element when the inhaled air volume reaches a first predetermined threshold, and wherein the controller is configured to turn off the nebulizer element when the inhaled air volume reaches a second predetermined threshold.

2. The nebulizer device of claim 1, wherein at least one of the first predetermined threshold and the second predetermined threshold is a patient-specific threshold.

3. The nebulizer device of claim 1 further comprising:
a removable storage container, the nebulizer device comprising a plurality of deposition detection elements configured to mate with a plurality of deposition identification elements disposed on the removable storage container.

4. The nebulizer device of claim 3, wherein the plurality of deposition detection elements are a plurality of detection pins.

5. The nebulizer device of claim 3, wherein the plurality of deposition identification elements are a plurality of metal contacts connected to the nebulizer element.

6. The nebulizer device of claim 5, wherein the plurality of deposition identification elements are indicative of a target deposition area within lungs of a patient.

7. The nebulizer device of claim 3, wherein an opening to the removable storage container is at least partly defined by the nebulizer element.

8. The nebulizer device of claim 7, wherein the nebulizer element is a nebulizer mesh.

9. The nebulizer device of claim 3, wherein the removable storage container comprises an interior cup nested within a chamber of the removable storage container.

10. The nebulizer device of claim 1 further comprising a one way valve positioned directly over the flow control sensor configured to permit airflow only in an upstream direction.

11. The nebulizer device of claim 1 further comprising:
a drip cup positioned between the mouthpiece and the flow control sensor.

12. The nebulizer device of claim 1 further comprising:
an exhalation valve positioned between the mouthpiece and the storage container.

13. The nebulizer device of claim 1 further comprising:
a portable power source coupled to the controller and nebulizer element, and stored within a housing of the nebulizer device.

14. The nebulizer device of claim 1 further comprising:
a status indicator coupled to the controller and comprising at least one of a light indicator and an auditory indicator.

15. The nebulizer device of claim 14, wherein the status indicator is configured to activate when the inhaled air volume reaches the first predetermined threshold.

16. The nebulizer device of claim 13, wherein the status indicator is configured to activate when the inhaled air volume reaches a second predetermined threshold.

17. The nebulizer device of claim 13, wherein the nebulizer device is a handheld device.

18. A method for targeted delivery of aerosolized particles to the lungs comprising:
providing the nebulizer device of claim 1;
determining a deposition identity from the removable storage container;
measuring and integrating an inspiratory flow to determine inspiratory volume;
activating the nebulizer element when the inspiratory volume reaches a first volume threshold associated with the deposition identity; and
deactivating the nebulizer element when the inspiratory volume reaches a second volume threshold associated with the deposition identity.

19. The nebulizer device of claim 1, wherein the variable orifice is configured to increase resistance sensitivity as airflow increases.

* * * * *